(12) United States Patent
Zhang et al.

(10) Patent No.: US 11,918,980 B2
(45) Date of Patent: Mar. 5, 2024

(54) CATALYST FOR CONTINUOUS PRODUCTION OF 1,1,1,3-TETRACHLOROPROPANE THROUGH GAS-SOLID REACTION AS WELL AS PREPARATION METHOD AND USE THEREOF

(71) Applicants: NINGBO INSTITUTE OF MATERIALS TECHNOLOGY AND ENGINEERING, CHINESE ACADEMY OF SCIENCES, Ningbo (CN); NINGBO JUHUA CHEMICAL & SCIENCE CO., LTD., Ningbo (CN)

(72) Inventors: Yexin Zhang, Ningbo (CN); Qiang Zhou, Ningbo (CN); Jian Zhang, Ningbo (CN); Junliang Zhong, Ningbo (CN); Xiuxiu Wang, Ningbo (CN); Jili Du, Ningbo (CN); Hui Chen, Ningbo (CN); Chengjun Mu, Ningbo (CN); Jie Yang, Ningbo (CN); Linbing Xia, Ningbo (CN); Yong Yang, Ningbo (CN); Gang Wu, Ningbo (CN)

(73) Assignees: NINGBO INSTITUTE OF MATERIALS TECHNOLOGY & ENGINEERING, CHINESE ACADEMY OF SCIENCES, Ningbo (CN); NINGBO JUHUA CHEMICAL & SCIENCE CO., LTD., Ningbo (CN)

( * ) Notice: Subject to any disclaimer, the term of this patent is extended or adjusted under 35 U.S.C. 154(b) by 0 days.

(21) Appl. No.: 18/258,332

(22) PCT Filed: Dec. 24, 2021

(86) PCT No.: PCT/CN2021/141027
§ 371 (c)(1),
(2) Date: Jun. 20, 2023

(87) PCT Pub. No.: WO2023/108788
PCT Pub. Date: Jun. 22, 2023

(65) Prior Publication Data
US 2024/0001346 A1    Jan. 4, 2024

(30) Foreign Application Priority Data

Dec. 17, 2021  (CN) .......................... 202111550988.5

(51) Int. Cl.
 *B01J 23/745*   (2006.01)
 *B01J 21/18*    (2006.01)
 (Continued)

(52) U.S. Cl.
 CPC ............. *B01J 23/745* (2013.01); *B01J 21/18* (2013.01); *B01J 35/023* (2013.01); *B01J 37/088* (2013.01);
 (Continued)

(58) Field of Classification Search
 CPC ........ B01J 23/745; B01J 21/18; B01J 35/023; B01J 37/088; C07C 17/354; C07C 2523/745
 (Continued)

(56) References Cited

U.S. PATENT DOCUMENTS 4,535,194 A * 8/1985 Woodard ................ C07C 17/25
570/228
4,650,914 A * 3/1987 Woodard .............. C07C 17/275
570/228

(Continued)

FOREIGN PATENT DOCUMENTS

CN    1986507    *   6/2007
CN    1986507 A       6/2007
(Continued)

OTHER PUBLICATIONS

English translation of Written Opinion for PCT/CN2021/141027. (Year: 2022).*

(Continued)

Primary Examiner — Patricia L. Hailey
(74) Attorney, Agent, or Firm — Bayramoglu Law Offices LLC

(57) ABSTRACT

A catalyst for continuous production of 1,1,1,3-tetrachloropropane through gas-solid reaction as well as a preparation method and use thereof are provided. The catalyst includes a zero-valent iron and phosphorus co-modified carbon material which includes a carbon material as a carrier, a zero-valent iron supported onto the carrier and serving as an active component, and a phosphate functional group formed on the surface of the carbon material. The preparation method includes: co-modifying a carbon material using a ferric salt and organic phosphorus to obtain the catalyst for continuous production of 1,1,1,3-tetrachloropropane through gas-solid reaction. The present application further provides a method for continuous production of 1,1,1,3-tetrachloropropane through gas-solid reaction. The catalyst provided in the present application integrates active component zero-valent iron and auxiliary component phosphate functional group on the carbon material, thereby realizing the continuous production of 1,1,1,3-tetrachloropropane on a gas-solid fixed bed reactor.

20 Claims, 1 Drawing Sheet

(51) Int. Cl.
*B01J 35/02* (2006.01)
*B01J 37/08* (2006.01)
*C07C 17/354* (2006.01)

(52) U.S. Cl.
CPC ...... *C07C 17/354* (2013.01); *C07C 2523/745* (2013.01)

(58) Field of Classification Search
USPC .................. 502/182, 208, 213, 338, 185
See application file for complete search history.

(56) References Cited

U.S. PATENT DOCUMENTS

| | | | | |
|---|---|---|---|---|
| 5,529,968 | A * | 6/1996 | Sudhakar | B01J 27/188 502/185 |
| 8,487,146 | B2 * | 7/2013 | Wilson | C07C 17/25 570/220 |
| 2011/0237843 | A1 * | 9/2011 | Tung | C07C 17/206 570/151 |
| 2021/0009490 | A1 | 1/2021 | Myers | |
| 2022/0081379 | A1 * | 3/2022 | Lv | B01D 67/0088 |

FOREIGN PATENT DOCUMENTS

| | | | |
|---|---|---|---|
| CN | 109476567 | A * | 3/2019 |
| CN | 110813337 | * | 2/2020 |
| CN | 110813337 | A | 2/2020 |
| CN | 111056913 | * | 4/2020 |
| CN | 111056913 | A | 4/2020 |
| CN | 114605226 | A * | 6/2022 |
| EP | 0131561 | A1 * | 1/1985 |
| WO | 2016128763 | A1 | 8/2016 |
| WO | 2018022500 | A1 | 2/2018 |
| WO | 2020133554 | A1 | 7/2020 |

OTHER PUBLICATIONS

English translation of Search Report for PCT/CN2021/141027. (Year: 2022).*
R. M. Joyce et al., "Free Radical-initiated Reaction of Ethylene with Carbon Tetrachloride." Journal of the American Chemical Society, vol. 70, Issue 7, pp. 2529-2532. (Year: 1948).*

* cited by examiner

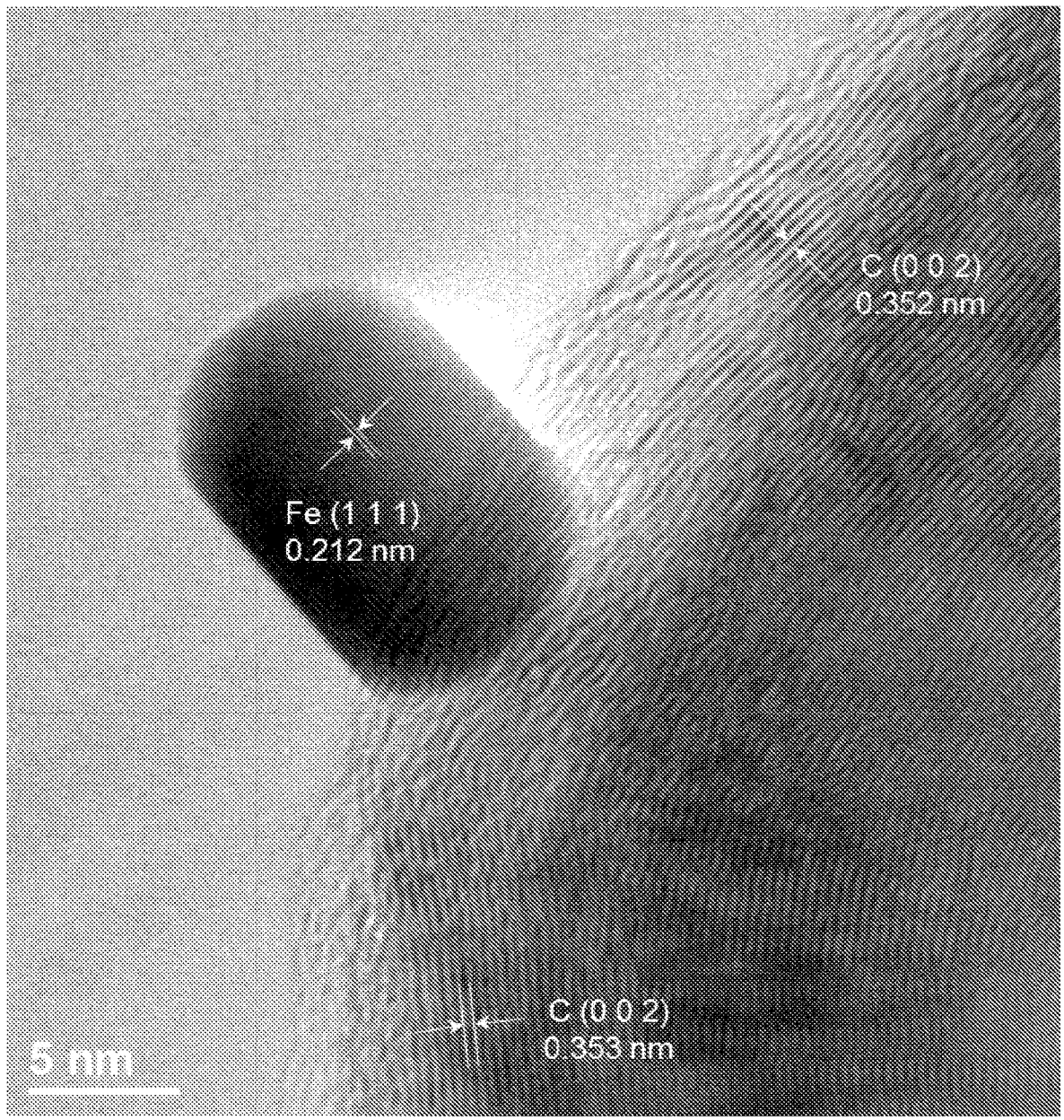

CATALYST FOR CONTINUOUS PRODUCTION OF 1,1,1,3-TETRACHLOROPROPANE THROUGH GAS-SOLID REACTION AS WELL AS PREPARATION METHOD AND USE THEREOF

CROSS REFERENCE TO THE RELATED APPLICATIONS

This patent application is the national phase entry of International Application No. PCT/CN2021/141027, filed on Dec. 24, 202, which claims priority to Chinese Patent Application No. 202111550988.5, filed on Dec. 17, 2021, the entire contents of which are incorporated herein by reference.

TECHNICAL FIELD

The present application relates to a catalyst for production of 1,1,3-tetrachloropropane, particularly to a catalyst for continuous production of 1,1,1,3-tetrachloropropane through gas-solid reaction as well as a preparation method and use thereof, belonging to the technical field of chemical industry.

BACKGROUND 1,1,1,3-tetrachloropropane is an important fine chemical, which is an important raw material for synthesizing paint removers, degreasers and various fluorosilicone products, and therefore has a huge market potential. This chemical is obtained by catalyzing oligomerization based on tetrachloromethane and ethylene as raw materials. The common catalytic systems are categorized as iron powder-ferric (ferrous) chloride-alkyl (methylene) phosphate, iron powder-alkyl (methylene) phosphate, alkyl (methylene) phosphate-ferric chloride-alkyl nitrile and copper powder-alkyl nitrile. In these systems, the cocatalyst alkyl (methylene) phosphate or alkyl nitrile is liquid, which is absolutely necessary in a reaction. Thus, the current synthesis of 1,1,1,3-tetrachloropropane can only adopt batch tank reaction. However, the batch tank reaction has the problems of difficult separation and long production time of the catalyst, limited yield per tank and wasted energy consumption in the processes of heating and cooling, and therefore it is low in production efficiency and is not suitable for industrialized large-scale production of products. Therefore, there is a lack of a solid catalyst and method for continuous production of 1,1,1,3-tetrachloropropane by gas-solid reaction in the art.

SUMMARY

The main objective of the present application is to provide a catalyst for continuous production of 1,1,1,3-tetrachloropropane through gas-solid reaction and a preparation method thereof, thereby overcoming the defects in the prior art.

Another objective of the present disclosure is to provide a method for continuous production of 1,1,1,3-tetrachloropropane through gas-solid reaction.

In order to realize the above objectives, the present application adopts the following technical solution:

The embodiments of the present application provide a catalyst for continuous production of 1,1,1,3-tetrachloropropane through gas-solid reaction. The catalyst comprises a zero-valent iron and phosphorus co-modified carbon material which comprises a carbon material as a carrier, a zero-valent iron supported onto the carrier and serving as an active component, and a phosphate functional group formed on the surface of the carbon material The embodiments of the present application further provide a preparation method of a catalyst for continuous production of 1,1,1,3-tetrachloropropane through gas-solid reaction, comprising: co-modifying a carbon material by using a ferric salt and organic phosphorus to obtain the catalyst for continuous production of 1,1,1,3-tetrachloropropane through gas-solid reaction.

In some embodiments, the preparation method specifically comprises:
  heating a first mixture comprising the carbon material and the ferric salt to 600-1000° C. at the temperature raising rate of 5° C./min-10° C./min in an inert atmosphere to be roasted for 1-4 h to obtain a zero-valent iron modified carbon material; and
  heating a second mixture comprising the zero-valent iron modified carbon material and organic phosphorus to 600-1000° C. in an inert atmosphere to be roasted for 1-4 h to obtain the catalyst for continuous production of 1,1,1,3-tetrachloropropane through gas-solid reaction.

In other embodiments, the preparation method specifically comprises:
  heating a third mixture comprising the carbon material and organic phosphorus to 600-1000° C. at the temperature raising rate of 5° C./min-10° C./min in an inert atmosphere to be roasted for 1-4 h to obtain a phosphorus modified carbon material; and
  sufficiently contacting the phosphorous modified carbon material with a solution containing the ferric salt for 4-6 h, and adding a reducing agent in an inert atmosphere to at least reduce iron ions into zero-valent iron, so as to obtain the catalyst for continuous production of 1,1,1,3-tetrachloropropane through gas-solid reaction.

The embodiments of the present application further provide use of the catalyst for continuous production of 1,1,1, 3-tetrachloropropane through gas-solid reaction in continuous production of 1,1,1,3-tetrachloropropane.

Correspondingly, the embodiments of the present application further provide a method for continuous production of 1,1,1,3-tetrachloropropane through gas-solid reaction, comprising:
  encapsulating the catalyst for continuous production of 1,1,1,3-tetrachloropropane through gas-solid reaction in a gas-solid fixed bed reactor to form a catalyst bed layer; and
  continuously introducing reaction raw material gas comprising carbon tetrachloride and ethylene into the catalyst bed layer, wherein the inlet pressure of the reaction raw material gas is increased to 0.8-1.2 MPa and the temperature of heating the catalyst bed layer is increased to 80-120° C., and then catalyzing oligomerization to obtain 1,1,1,3-tetrachloropropane.

Compared with the prior art, the present application at least has the beneficial effects:

The catalyst provided in the present application uses the carbon material as the carrier, an active component zero-valent iron is supported onto the carrier to replace primary catalyst iron powders in the existing tank reaction; the auxiliary component phosphate functional group is formed on the surface of the carbon material through phosphorus modification to replace the cocatalyst alkyl phosphate in the existing tank reaction, thereby getting rid of the dependence of the traditional batch tank reaction on the liquid cocatalyst. Thus, in the present application, the primary catalyst (zero-valent iron) and the cocatalyst (phosphate functional group)

are integrated on the carbon material to serve as a single solid catalyst which can be directly used for synthesis of 1,1,1,3-tetrachloropropane. Without the use of the liquid cocatalyst, this solid catalyst can be directly encapsulated in the gas-solid fixed bed reactor, and then raw materials carbon tetrachloride and ethylene are continuously introduced into the reactor, subsequently the continuous synthesis of 1,1,1,3-tetrachloropropane can be achieved under the conditions of pressurizing and heating.

BRIEF DESCRIPTION OF THE DRAWINGS

To more clearly explain the technical solution in the embodiments of the present application or in the prior art, accompanying drawings required to be used in the embodiments or in the prior art will be simply discussed. Obviously, the drawings described hereinafter are only some embodiments described in the present application, other drawings can also be obtained by persons of ordinary skill in the art without creative efforts according to these drawings.

The FIGURE is a microstructure graph of a zero-valent iron and phosphorus co-modified activated carbon catalyst in example 1 of the present application.

DETAILED DESCRIPTION OF THE EMBODIMENTS

In view of the defects in the prior art, the inventors of this case propose the technical solution of the present application by long-term researches and lots of practices. Next, the technical solution, its implementation process and principle will be further explained.

A catalyst for continuous production of 1,1,1,3-tetrachloropropane through gas-solid reaction provided according to one aspect of the embodiments of the present application is a zero-iron and phosphorus co-modified carbon material. The zero-iron and phosphorus co-modified carbon material comprises a carbon material as a carrier, a zero-valent iron supported onto the carrier and serving as an active component, and a phosphate functional group formed on the surface of the carbon material.

In some embodiments, the mass content of iron in the catalyst is 1-10 wt %, and the mass content of phosphorus in the catalyst is 1-10 wt %.

In some embodiments, the particle size of zero-valent iron in the catalyst is 2-100 nm.

In some embodiments, the carbon material comprises at least one of activated carbon, a carbon nanotube and graphene, but is not limited thereto.

Another aspect of the embodiments of the present application further provides a preparation method of a catalyst for continuous production of 1,1,1,3-tetrachloropropane through gas-solid reaction, comprising: co-modifying a carbon material by using a ferric salt and organic phosphorus to obtain the catalyst for continuous production of 1,1,1,3-tetrachloropropane through gas-solid reaction.

In some embodiments, the preparation method of the catalyst specifically comprises:
heating a first mixture comprising the carbon material and the ferric salt to 600-1000° C. at the temperature raising rate of 5° C./min-10° C./min in an inert atmosphere to be roasted for 1-4 h to obtain a zero-valent iron modified carbon material; and
heating a second mixture comprising the zero-valent iron modified carbon material and organic phosphorus to 600-1000° C. in an inert atmosphere to be roasted for 1-4 h to obtain the catalyst for continuous production of 1,1,1,3-tetrachloropropane through gas-solid reaction.

In some specific embodiments, one step for synthesizing the catalyst is as follows:
(1) mixing the carbon material with the ferric salt, heating to 600-1000° C. at the temperature raising rate of 5° C./min-10° C./min in an inert atmosphere to be roasted for 1-4 h, and then cooling to room temperature so as to obtain the zero-valent iron modified carbon material; and
(2) mixing the zero-valent iron modified carbon material obtained in step (1) with organic phosphorus, heating to 600-1000° C. in an inert atmosphere to be roasted for 1-4 h, and then cooling to room temperature so as to obtain the catalyst.

In some embodiments, another method for synthesizing the catalyst specifically comprises:
heating a third mixture comprising the carbon material and organic phosphorus to 600-1000° C. at the temperature raising rate of 5° C./min-10° C./min in an inert atmosphere to be roasted for 1-4 h to obtain a phosphorus modified carbon material; and
sufficiently contacting the phosphorous modified carbon material with a solution containing the ferric salt, and adding a reducing agent in an inert atmosphere to at least reduce iron ions into zero-valent iron, so as to obtain the catalyst for continuous production of 1,1,1,3-tetrachloropropane through gas-solid reaction.

Further, the reducing agent comprises sodium borohydride ($NaBH_4$) and potassium borohydride ($KBH_4$), but is not limited thereto.

In other specific embodiments, another steps for synthesizing the catalyst are as follows:
(1) mixing the carbon material with organic phosphorus, heating to 600-1000° C. at the temperature raising rate of 5° C./min-10° C./min in an inert atmosphere to be roasted for 1-4 h, and then cooling to room temperature so as to obtain the phosphorus modified carbon material;
(2) soaking the phosphorus modified carbon material obtained in step (1) into a ferric salt solution, and adding sodium borohydride or potassium borohydride in an inert atmosphere to reduce iron ions into zero-valent iron.
(3) filtering, washing and drying to obtain the catalyst.

Further, the concentration of sodium borohydride or potassium borohydride in the reaction system in step (2) is 0.2 mol/L-0.4 mol/L.

In some embodiments, the carbon material comprises at least one of activated carbon, carbon nanotube and graphene, but is not limited thereto.

In some specific embodiments, the ferric salt comprises at least one of ferrous chloride, ferrous nitrate, ferrous sulfate, ferric nitrate nonahydrate and ferric chloride, but is not limited thereto.

Further, a molar ratio of the carbon material to the ferric salt is 11:1-112:1.

Further, a molar ratio of a carbon element in the carbon material or zero-valent iron modified carbon material to a phosphorus element in organic phosphorus is 3:1-7:1.

Further, the concentration of the ferric salt in the solution containing the ferric salt is 0.1 mol/L-1.8 mol/L.

In some specific embodiments, the organic phosphorus comprises at least one of phenylphosphine dichloride, diphenylphosphine, triphenylphosphine, diphenyl(p-tolyl)phosphine and diphenylcyclohexyl phosphine, but is not limited thereto.

Another aspect of the embodiments of the present application further provides the catalyst for continuous production of 1,1,1,3-tetrachloropropane through gas-solid reaction prepared by the above-mentioned method.

Another aspect of the embodiments of the present application further provides use of the catalyst for continuous production of 1,1,1,3-tetrachloropropane through gas-solid reaction in continuous production of 1,1,1,3-tetrachloropropane.

Correspondingly, another aspect of the embodiments of the present application further provides a method for continuous production of 1,1,1,3-tetrachloropropane through gas-solid reaction, comprising: encapsulating a catalyst in a gas-solid fixed bed reactor, continuously introducing raw material gas comprising carbon tetrachloride and ethylene at a certain pressure under a certain temperature, and then catalyzing oligomerization to obtain a 1,1,1,3-tetrachloropropane product.

In some specific embodiments, the method specifically comprises:
  encapsulating the catalyst for continuous production of 1,1,1,3-tetrachloropropane through gas-solid reaction in the gas-solid fixed bed reactor to form a catalyst bed layer; and
  continuously introducing reaction raw material gas comprising carbon tetrachloride and ethylene into the catalyst bed layer, wherein the inlet pressure of the reaction raw material gas is increased to 0.8-1.2 MPa and the temperature of heating the catalyst bed layer is increased to 80-120° C., and then catalyzing oligomerization to obtain 1,1,1,3-tetrachloropropane, and collecting the 1,1,1,3-tetrachloropropane product at the tail end of the fixed bed.

Further, a volume ratio of carbon tetrachloride to ethylene is 1:2-2:1.

In summary, the catalyst of the present application integrates the active component zero-valent iron and the auxiliary component phosphate functional group on the carbon material, thereby getting rid of the dependence of the traditional batch tank reaction on the cocatalyst and realizing the continuous production of 1,1,1,3-tetrachloropropane on the gas-solid fixed bed reactor.

To better illustrate the purpose, technical solution and advantages of the present application, the technical solution of the present application will be explained in detail in combination with several preferred embodiments below. The following specific embodiments are only for further illustrating and explaining the present application, but not limiting the present application; all the deformations considered or derived from the contents disclosed in the present application are included within the protective scope of the present application.

Example 1

50 g of activated carbon was mixed with 50 g of ferric nitrate nonahydrate, the obtained mixture was heated to 800° C. at the temperature raising rate of 8° C./min in a nitrogen atmosphere to be roasted for 3 hours and then cooled to room temperature to obtain zero-valent iron modified activated carbon, then the zero-valent iron modified activated carbon was mixed with 100 g of triphenylphosphine followed by roasting the obtained mixture for 3 hours at 900° C. in a nitrogen atmosphere to obtain a zero-valent iron and phosphorus co-modified activated carbon catalyst. By element analysis, it is concluded that in this catalyst, the mass content of iron is 3 wt %, the mass content of phosphorus is 8 wt %, and the particle size of zero-valent iron is 2-100 nm. By observing the micromorphology of the catalyst through high resolution electron transmission microscopy, it can be seen that the size of zero-valent iron particles embedded into a graphite carbon layer is 13 nm (as shown in The FIGURE).

Example 2

50 g of graphene was mixed with 20 g of ferric chloride, the obtained mixture was heated to 1000° C. at the temperature raising rate of 10° C./min in a nitrogen atmosphere to be roasted for 2 hours and then cooled to room temperature to obtain zero-valent iron modified graphene, then the zero-valent iron modified graphene was mixed with 110 g of diphenyl(p-tolyl)phosphine followed by roasting the obtained mixture for 3 hours at 900° C. in a nitrogen atmosphere to obtain a zero-valent iron and phosphorus co-modified graphene catalyst. By element analysis, it is concluded that in this catalyst, the mass content of iron is 2 wt %, and the mass content of phosphorus is 4 wt %.

Example 3

50 g of carbon nanotube was mixed with 200 g of dichlorophenyl phosphine, the obtained mixture was heated to 1000° C. at the temperature raising rate of 6° C./min in a nitrogen atmosphere to be roasted for 1 hour to obtain a phosphorus modified carbon nanotube, then the phosphorus modified carbon nanotube was soaked into 1 L of aqueous solution containing 50 g of ferrous chloride, the above mixed solution was adjusted with hydrochloric acid until pH<3, nitrogen was introduced, then 1 L of aqueous solution containing 50 g of sodium borohydride was dropwise added while stirring for 4 hours, and then the obtained mixed solution was filtered, washed and dried to obtain a zero-valent iron and phosphorus co-modified carbon nanotube catalyst. By element analysis, it is concluded that in this catalyst, the mass content of iron is 8 wt %, and the mass content of phosphorus is 5 wt %.

Example 4

50 g of activated carbon was mixed with 50 g of ferrous nitrate, the obtained mixture was heated to 600° C. at the temperature raising rate of 5° C./min in a nitrogen atmosphere to be roasted for 1 hour and then cooled to room temperature to obtain zero-valent iron modified activated carbon, then the zero-valent iron modified activated carbon was mixed with 100 g of diphenyl phosphine followed by roasting the obtained mixture for 3 hours at 900° C. in a nitrogen atmosphere to obtain a zero-valent iron and phosphorus co-modified activated carbon catalyst. By element analysis, it is concluded that in this catalyst, the mass content of iron is 3 wt %, and the mass content of phosphorus is 7 wt %.

Example 5

50 g of graphene was mixed with 20 g of ferrous chloride, the obtained mixture was heated to 1000° C. at the temperature raising rate of 8° C./min to be roasted for 2 hours and then cooled to room temperature to obtain zero-valent iron modified graphene, then the zero-valent iron modified graphene was mixed with 110 g of diphenylcyclohexyl phosphine followed by roasting the obtained mixture for 1 hour at 1000° C. in a nitrogen atmosphere to obtain a zero-valent iron and phosphorus co-modified graphene catalyst. By element analysis, it is concluded that in this catalyst, the mass content of iron is 2 wt %, and the mass content of phosphorus is 3 wt %.

Example 6

50 g of carbon nanotube was mixed with 200 g of dichlorophenyl phosphine, the obtained mixture was heated to 600° C. at the temperature raising rate of 5° C./min in a nitrogen atmosphere to be roasted for 4 hours to obtain a phosphorus modified carbon nanotube, then the phosphorus modified carbon nanotube was soaked into 1 L of aqueous solution containing 50 g of ferrous nitrate, the above mixed solution was adjusted with hydrochloric acid until pH<3, nitrogen was introduced, then 1 L of aqueous solution containing 50 g of potassium borohydride was dropwise added while stirring for 6 hours, and then the obtained mixed solution was filtered, washed and dried to obtain a zero-valent iron and phosphorus co-modified carbon nanotube catalyst. By element analysis, it is concluded that in this catalyst, the mass content of iron is 8 wt %, and the mass content of phosphorus is 6 wt %.

Example 7

50 g of graphene was mixed with 20 g of ferrous sulfate, the obtained mixture was heated to 1000° C. at the temperature raising rate of 10° C./min to be roasted for 2 hours and then cooled to room temperature to obtain zero-valent iron modified graphene, then the zero-valent iron modified graphene was mixed with 110 g of diphenyl(p-tolyl)phosphine followed by roasting the obtained mixture for 4 hours at 600° C. in a nitrogen atmosphere to obtain a zero-valent iron and phosphorus co-modified graphene catalyst. By element analysis, it is concluded that in this catalyst, the mass content of iron is 2 wt %, and the mass content of phosphorus is 5 wt %.

Example 8

A gas-solid fixed bed reactor in this example adopts an electrically heated tubular reactor with a tube diameter of 10 millimeters and a length of 0.5 meter. The reaction process was as follows:
(1) putting 20 g of zero-valent iron and phosphorus activated carbon catalyst prepared in example 1 into a reaction tube;
(2) preheating carbon tetrachloride at 85° C. and then simultaneously introducing preheated carbon tetrachloride and ethylene into the reaction tube, wherein a volume ratio of carbon tetrachloride to ethylene was 1:1, and the total flow was 20 mL/min;
(3) adjusting an inlet pressure to 0.9 MPa;
(4) heating the temperature of a catalyst bed layer to 100° C.; and
(5) collecting a 1,1,1,3-tetrachloropropane crude product at the tail end of a fixed bed.

The product obtained in this example was subjected to gas chromatography. As can be seen, the conversion rate of carbon tetrachloride is 70%, and the selectivity of 1,1,1,3-tetrachloropropane is 99%.

Example 9

A gas-solid fixed bed reactor in this example adopts an electrically heated tubular reactor with a tube diameter of 10 millimeters and a length of 0.5 meter. The reaction process was as follows:
(1) putting 20 g of zero-valent iron and phosphorus activated carbon catalyst prepared in example 1 into a reaction tube;
(2) preheating carbon tetrachloride at 85° C. and then simultaneously introducing preheated carbon tetrachloride and ethylene into the reaction tube, wherein a volume ratio of carbon tetrachloride to ethylene was 1:2, and the total flow was 20 mL/min;
(3) adjusting an inlet pressure to 0.8 MPa;
(4) heating the temperature of a catalyst bed layer to 100° C.; and
(5) collecting a 1,1,1,3-tetrachloropropane crude product at the tail end of a fixed bed.

The product obtained in this example was subjected to gas chromatography. As can be seen, the conversion rate of carbon tetrachloride is 68%, and the selectivity of 1,1,1,3-tetrachloropropane is 98.9%.

Example 10

A gas-solid fixed bed reactor in this example adopts an electrically heated tubular reactor with a tube diameter of 10 millimeters and a length of 0.5 meter. The reaction process was as follows:
(1) putting 20 g of zero-valent iron and phosphorus co-modified activated carbon catalyst prepared in example 1 into a reaction tube;
(2) preheating carbon tetrachloride at 85° C. and then simultaneously introducing preheated carbon tetrachloride and ethylene into the reaction tube, wherein a volume ratio of carbon tetrachloride to ethylene was 2:1, and the total flow was 20 mL/min;
(3) adjusting an inlet pressure to 1.2 MPa;
(4) heating the temperature of a catalyst bed layer to 100° C.; and
(5) collecting a 1,1,1,3-tetrachloropropane crude product at the tail end of a fixed bed.

The product obtained in this example was subjected to gas chromatography. As can be seen, the conversion rate of carbon tetrachloride is 72%, and the selectivity of 1,1,1,3-tetrachloropropane is 99.3%.

Example 11

A gas-solid fixed bed reactor in this example adopts an electrically heated tubular reactor with a tube diameter of 10 millimeters and a length of 0.5 meter. The reaction process was as follows:
(1) putting 20 g of zero-valent iron and phosphorus co-modified activated carbon catalyst prepared in example 1 into a reaction tube;
(2) preheating carbon tetrachloride at 85° C. and then simultaneously introducing preheated carbon tetrachloride and ethylene into the reaction tube, wherein a volume ratio of carbon tetrachloride to ethylene was 1:1, and the total flow was 20 mL/min;
(3) adjusting an inlet pressure to 0.9 MPa;
(4) heating the temperature of a catalyst bed layer to 80° C.; and
(5) collecting a 1,1,1,3-tetrachloropropane crude product at the tail end of a fixed bed.

The product obtained in this example was subjected to gas chromatography. As can be seen, the conversion rate of carbon tetrachloride is 67%, and the selectivity of 1,1,1,3-tetrachloropropane is 98.4%.

Example 12

A gas-solid fixed bed reactor in this example adopts an electrically heated tubular reactor with a tube diameter of 10 millimeters and a length of 0.5 meter. The reaction process was as follows:
(1) putting 20 g of zero-valent iron and phosphorus co-modified activated carbon catalyst prepared in example 1 into a reaction tube;
(2) preheating carbon tetrachloride at 85° C. and then simultaneously introducing preheated carbon tetrachloride and ethylene into the reaction tube, wherein a volume ratio of carbon tetrachloride to ethylene was 1:1, and the total flow was 20 mL/min;
(3) adjusting an inlet pressure to 0.9 MPa;
(4) heating the temperature of a catalyst bed layer to 120° C.; and
(5) collecting a 1,1,1,3-tetrachloropropane crude product at the tail end of a fixed bed.

The product obtained in this example was subjected to gas chromatography. As can be seen, the conversion rate of carbon tetrachloride is 71%, and the selectivity of 1,1,1,3-tetrachloropropane is 98.8%.

Example 13

The fixed bed reactor in example 8 was utilized, and the reaction process was as follows:
(1) putting 20 g of zero-valent iron and phosphorus co-modified carbon nanotube catalyst prepared in example 3 into a reaction tube;
(2) preheating carbon tetrachloride at 85° C. and then simultaneously introducing preheated carbon tetrachloride and ethylene into the reaction tube, wherein a volume ratio of carbon tetrachloride to ethylene was 1:1, and the total flow was 20 mL/min;
(3) adjusting an inlet pressure to 1 MPa;
(4) heating the temperature of a catalyst bed layer to 110° C.; and
(5) collecting a 1,1,1,3-tetrachloropropane crude product at the tail end of a fixed bed.

The product obtained in this example was subjected to gas chromatography. As can be seen, the conversion rate of carbon tetrachloride is 45%, and the selectivity of 1,1,1,3-tetrachloropropane is 97%.

Example 14

The fixed bed reactor in example 8 was utilized, and the reaction process was as follows:
(1) putting 20 g of zero-valent iron and phosphorus co-modified activated carbon catalyst prepared in example 4 into a reaction tube;
(2) preheating carbon tetrachloride at 85° C. and then simultaneously introducing preheated carbon tetrachloride and ethylene into the reaction tube, wherein a volume ratio of carbon tetrachloride to ethylene was 1:2, and the total flow was 20 mL/min;
(3) adjusting an inlet pressure to 0.8 MPa;
(4) heating the temperature of a catalyst bed layer to 90° C.; and
(5) collecting a 1,1,1,3-tetrachloropropane crude product at the tail end of a fixed bed.

The product obtained in this example was subjected to gas chromatography. As can be seen, the conversion rate of carbon tetrachloride is 65%, and the selectivity of 1,1,1,3-tetrachloropropane is 96%.

Example 15

The fixed bed reactor in example 8 was utilized, and the reaction process was as follows:
(1) putting 20 g of zero-valent iron and phosphorus co-modified carbon nanotube catalyst prepared in example 6 into a reaction tube;
(2) preheating carbon tetrachloride at 85° C. and then simultaneously introducing preheated carbon tetrachloride and ethylene into the reaction tube, wherein a volume ratio of carbon tetrachloride to ethylene was 1:1 and the total flow was 20 mL/min;
(3) adjusting an inlet pressure to 1.2 MPa;
(4) heating the temperature of a catalyst bed layer to 120° C.; and
(5) collecting a 1,1,1,3-tetrachloropropane crude product at the tail end of a fixed bed.

The product obtained in this example was subjected to gas chromatography. As can be seen, the conversion rate of carbon tetrachloride is 52%, and the selectivity of 1,1,1,3-tetrachloropropane is 98%.

Example 16

The fixed bed reactor in example 8 was utilized, and the reaction process was as follows:
(1) putting 20 g of zero-valent iron and phosphorus co-modified carbon nanotube catalyst prepared in example 6 into a reaction tube;
(2) preheating carbon tetrachloride at 85° C. and then simultaneously introducing preheated carbon tetrachloride and ethylene into the reaction tube, wherein a volume ratio of carbon tetrachloride to ethylene was 2:1 and the total flow was 20 mL/min;
(3) adjusting an inlet pressure to 1.2 MPa;
(4) heating the temperature of a catalyst bed layer to 120° C.; and
(5) collecting a 1,1,1,3-tetrachloropropane crude product at the tail end of a fixed bed.

The product obtained in this example was subjected to gas chromatography. As can be seen, the conversion rate of carbon tetrachloride is 52%, and the selectivity of 1,1,1,3-tetrachloropropane is 98%.

In addition, the inventors also conducted tests with other raw materials, process operations and process conditions described in this specification with reference to the above-mentioned examples, and obtained relatively ideal results.

Comparative Example 1

This comparative example is different from example 1 in that only phosphorus modified activated carbon catalyst is prepared without addition of ferric nitrate nonahydrate.

When the phosphorus modified activated carbon catalyst in this comparative example is used for example 8, the conversion rate of carbon tetrachloride is 27%, and the selectivity of 1,1,1,3-tetrachloropropane is 41%.

Comparative Example 2

This comparative example is different from example 1 in that only zero-valent iron modified activated carbon catalyst is prepared without addition of triphenylphosphine.

When the zero-valent iron modified activated carbon catalyst in this comparative example is used for example 8, the conversion rate of carbon tetrachloride is 54%, and the selectivity of 1,1,1,3-tetrachloropropane is 67%.

Comparative Example 3

This comparative example is different from example 3 in that only phosphorus modified activated carbon catalyst is prepared without addition of ferrous chloride.

When the phosphorus modified activated carbon catalyst in this comparative example is used for example 13, the conversion rate of carbon tetrachloride is 25%, and the selectivity of 1,1,1,3-tetrachloropropane is 56%.

Comparative Example 4

This comparative example is different from example 3 in that only zero-valent iron modified activated carbon catalyst is prepared without addition of dichlorophenyl phosphine.

When the zero-valent iron modified activated carbon catalyst in this comparative example is used for example 13, the conversion rate of carbon tetrachloride is 37%, and the selectivity of 1,1,1,3-tetrachloropropane is 60%.

In conclusion, the above descriptions are several embodiments of the present application but not limitation to the present application in any forms. Although the present application is disclosed as above in preferred embodiments, they are not intended to limit the present application. Some changes or modifications made by those skilled in the art without departing from the scope of the technical solution of the present application by utilizing the above disclosed technical contents are equivalent to embodiments and are all included within the scope of the technical solution.

What is claimed is:

1. A catalyst for continuous production of 1,1,1,3-tetrachloropropane through a gas-solid reaction, comprising a zero-valent iron and a phosphorus co-modified carbon material wherein the zero-valent iron and the phosphorus co-modified carbon material comprises a carbon material as a carrier, the zero-valent iron supported onto the carrier and the zero-valent iron is served as an active component, and a phosphate functional group formed on a surface of the carbon material.

2. The catalyst for continuous production of the 1,1,1,3-tetrachloropropane through gas-solid reaction according to claim 1, wherein in the catalyst, a content of iron is 1-10 wt %, and a content of phosphorus is 1-10 wt %.

3. The catalyst for continuous production of the 1,1,1,3-tetrachloropropane through the gas-solid reaction according to claim 1, wherein a particle size of the zero-valent iron in the catalyst is 2-100 nm.

4. The catalyst for continuous production of the 1,1,1,3-tetrachloropropane through the gas-solid reaction according to claim 1, wherein the carbon material comprises at least one of an activated carbon, a carbon nanotube, and graphene.

5. A preparation method of the catalyst for continuous production of the 1,1,1,3-tetrachloropropane through the gas-solid reaction according to claim 1, comprising:
co-modifying the carbon material using a ferric salt and an organic phosphorus to obtain the catalyst for continuous production of the 1,1,1,3-tetrachloropropane through the gas-solid reaction.

6. The preparation method according to claim 5, comprising:
heating a first mixture comprising the carbon material and the ferric salt to 600-1000° C. at a temperature raising rate of 5° C./min-10° C./min in an inert atmosphere to be roasted for 1-4 h to obtain a zero-valent iron modified carbon material; and
heating a second mixture comprising the zero-valent iron modified carbon material and the organic phosphorus to 600-1000° C. in the inert atmosphere to be roasted for 1-4 h to obtain the catalyst for continuous production of the 1,1,1,3-tetrachloropropane through the gas-solid reaction.

7. The preparation method according to claim 6, wherein a molar ratio of the carbon material to the ferric salt is 11:1-112:1;
and/or, a molar ratio of a carbon element in the carbon material or the zero-valent iron modified carbon material to a phosphorus element in the organic phosphorus is 3:1-7:1;
and/or, the carbon material comprises at least one of an activated carbon, a carbon nanotube and graphene;
and/or, the ferric salt comprises at least one of ferrous chloride, ferrous nitrate, ferrous sulfate, ferric nitrate, and ferric chloride;
and/or, a concentration of the ferric salt in a solution containing the ferric salt is 0.1 mol/L-1.8 mol/L;
and/or, the organic phosphorus comprises at least one of phenylphosphine dichloride, diphenylphosphine, triphenylphosphine, diphenyl(p-tolyl)phosphine and diphenylcyclohexyl phosphine.

8. The preparation method according to claim 5, comprising:
heating a third mixture comprising the carbon material and the organic phosphorus to 600-1000° C. at the temperature raising rate of 5° C./min-10° C./min in the inert atmosphere to be roasted for 1-4 h to obtain a phosphorus modified carbon material; and
sufficiently contacting the phosphorous modified carbon material with a solution containing the ferric salt for 4-6 h, and adding a reducing agent in the inert atmosphere to at least reduce iron ions into the zero-valent iron, so as to obtain the catalyst for continuous production of the 1,1,1,3-tetrachloropropane through the gas-solid reaction; the reducing agent comprises sodium borohydride and/or potassium borohydride.

9. The preparation method according to claim 8, wherein a molar ratio of the carbon material to the ferric salt is (11:1)-(112:1);
and/or, a molar ratio of a carbon element in the carbon material or the zero-valent iron modified carbon material to a phosphorus element in the organic phosphorus is 3:1-7:1;
and/or, the carbon material comprises at least one of an activated carbon, a carbon nanotube and graphene;
and/or, the ferric salt comprises at least one of ferrous chloride, ferrous nitrate, ferrous sulfate, ferric nitrate, and ferric chloride;
and/or, a concentration of the ferric salt in the solution containing the ferric salt is 0.1 mol/L-1.8 mol/L;
and/or, the organic phosphorus comprises at least one of phenylphosphine dichloride, diphenylphosphine, triphenylphosphine, diphenyl(p-tolyl)phosphine and diphenylcyclohexyl phosphine.

10. The preparation method according to claim 5, wherein in the catalyst, a content of iron is 1-10 wt %, and a content of phosphorus is 1-10 wt %.

11. The preparation method according to claim 5, wherein a particle size of the zero-valent iron in the catalyst is 2-100 nm.

12. The preparation method according to claim 5, wherein the carbon material comprises at least one of an activated carbon, a carbon nanotube, and graphene.

13. Use of the catalyst for continuous production of the 1,1,1,3-tetrachloropropane through gas-solid reaction according to claim 1 in continuous production of the 1,1,1,3-tetrachloropropane.

14. The use according to claim 13, wherein in the catalyst, a content of iron is 1-10 wt %, and a content of phosphorus is 1-10 wt %.

15. The use according to claim 13, wherein a particle size of the zero-valent iron in the catalyst is 2-100 nm.

16. The use according to claim 13, wherein the carbon material comprises at least one of an activated carbon, a carbon nanotube, and graphene.

17. A method for continuous production of the 1,1,1,3-tetrachloropropane through a gas-solid reaction, comprising:
encapsulating the catalyst for continuous production of the 1,1,1,3-tetrachloropropane through the gas-solid reaction according to claim 1 in a gas-solid fixed bed reactor to form a catalyst bed layer; and
continuously introducing a reaction raw material gas comprising carbon tetrachloride and ethylene into the catalyst bed layer, wherein an inlet pressure of the reaction raw material gas is increased to 0.8-1.2 MPa and a temperature of heating the catalyst bed layer is increased to 80-120° C., and then catalyzing oligomerization to obtain the 1,1,1,3-tetrachloropropane; a volume ratio of the carbon tetrachloride to the ethylene is 1:2-2:1.

18. The method according to claim 17, wherein in the catalyst, a content of iron is 1-10 wt %, and a content of phosphorus is 1-10 wt %.

19. The method according to claim 17, wherein a particle size of the zero-valent iron in the catalyst is 2-100 nm.

20. The method according to claim 17, wherein the carbon material comprises at least one of an activated carbon, a carbon nanotube, and graphene.

* * * * *